(12) United States Patent
Picard et al.

(10) Patent No.: US 11,823,473 B2
(45) Date of Patent: Nov. 21, 2023

(54) APPARATUS AND METHOD FOR CLASSIFYING PICTURES OF GEL-CARD REACTIONS

(71) Applicant: BIO-RAD EUROPE GMBH, Basel (CH)

(72) Inventors: Thomas Picard, Chazay d'Azergues (FR); Bruno De-Bastiani, Paris (FR); Jean-Baptiste Ballereau, Issy-les-Moulineaux (FR); Stephane Delaille, Saint-Cloud (FR); Eric Millet, Riorges (FR); Pierre Bony, Toulouse (FR); Olivier Noel, Ecuvillens (CH); Yves Raisin, Faoug (CH); Clément Foissac, Villarepos (CH)

(73) Assignee: BIO-RAD EUROPE GMBH, Basel (CH)

( * ) Notice: Subject to any disclaimer, the term of this patent is extended or adjusted under 35 U.S.C. 154(b) by 111 days.

(21) Appl. No.: 17/599,422

(22) PCT Filed: Mar. 26, 2020

(86) PCT No.: PCT/EP2020/025145
§ 371 (c)(1),
(2) Date: Sep. 28, 2021

(87) PCT Pub. No.: WO2020/192972
PCT Pub. Date: Oct. 1, 2020

(65) Prior Publication Data
US 2022/0189183 A1    Jun. 16, 2022

(30) Foreign Application Priority Data

Mar. 28, 2019 (EP) .................................. 19305401.2

(51) Int. Cl.
*G06K 9/00* (2022.01)
*G06V 20/69* (2022.01)
(Continued)

(52) U.S. Cl.
CPC ............ *G06V 20/698* (2022.01); *G06V 10/82* (2022.01); *G01N 2035/00148* (2013.01); *G01N 2035/00495* (2013.01)

(58) Field of Classification Search
None
See application file for complete search history.

(56) References Cited

U.S. PATENT DOCUMENTS

2015/0198591 A1*  7/2015  Patel ................ G01N 33/54313
                                                      435/7.25
2020/0378947 A1* 12/2020  Guignet .................... B01L 9/06

OTHER PUBLICATIONS

International Search Report and Written Opinion, Patent Cooperation Treaty Application No. PCT/EP2020/025145, dated June 22, 2020, 12 pages.

(Continued)

*Primary Examiner* — Soo Jin Park
(74) *Attorney, Agent, or Firm* — Fenwick & West LLP (57) ABSTRACT

An apparatus for classifying a picture of a reaction of reactants in a predetermined container; the apparatus comprising a first neural network arranged for receiving an input picture of a reaction of reactants in a predetermined container and for providing, for each reaction category of a first plurality of reaction categories, a probability that the input picture shows a reaction that belongs to said reaction category; a second neural network arranged for, if the first neural response provides a highest probability that the input picture shows a reaction that belongs to a predetermined reaction category, receiving a predetermined portion of the input picture and providing, for each reaction category of a second plurality of reaction categories, a probability that (Continued)

said predetermined portion of the input picture shows a reaction that belongs to said reaction category.

25 Claims, 5 Drawing Sheets

(51) Int. Cl.
    *G06V 10/82*     (2022.01)
    *G01N 35/00*     (2006.01)

(56)     References Cited

OTHER PUBLICATIONS

Nuno Miguel et al., "Faculdade De Engenharia Da Universidade Do Porto", Automatic blood typing scanner through agglutination, Jul. 11, 2014, retrieved from the Internet: URL:http://paginas.fe.up.pt/~ee07126/wp/files/dissertation_200707541.pdf; XP055201136; [retrieved on Jul. 8, 2015], the whole document.

Ferraz Ana et al., "Blood type classification using computer vision and machine learning", Jan. 13, 2016), Vol. 28, No. 8, p. 2029-2040, XP036274227; DOI: 10.1007/S00521-015-2151-1 ISSN:0941-0643; [retrieved on Jan. 13, 2016] [retrieved on Jan. 13, 2016], the whole document.

\* cited by examiner

APPARATUS AND METHOD FOR CLASSIFYING PICTURES OF GEL-CARD REACTIONS

CROSS-REFERENCE TO RELATED APPLICATIONS

This application is the National Stage entry of International Application No. PCT/EP2020/025145, filed on Mar. 26, 2020, which claims the right of priority to European Patent Application No. 19305401.2, filed on Mar. 28, 2019, both of which are incorporated by reference.

TECHNICAL FIELD

This presentation relates to apparatuses and methods using a plurality of neural networks for classifying pictures; more particularly pictures of agglutination reactions such as agglutination reactions taking place in gel cards.

BACKGROUND

A known manner of testing blood, for example for determining the blood type of a blood sample, comprises introducing the blood sample in a container filled with a separation matrix, for example a gel such as a dextran acrylamide gel, topped with a fluid that may contain a reagent (capable of complexing with an analyte to be detected in a blood sample) and/or a reticulation agent (capable of cross linking sensitized red blood cells or sensitized latex particles) such as a secondary antibody (e.g., anti-human globulin or anti-human IgA antibody), incubating the container and then centrifuging the container; where the location of agglutinated red blood cells in the gel provides information of the type of the tested blood sample.

Figure 1:
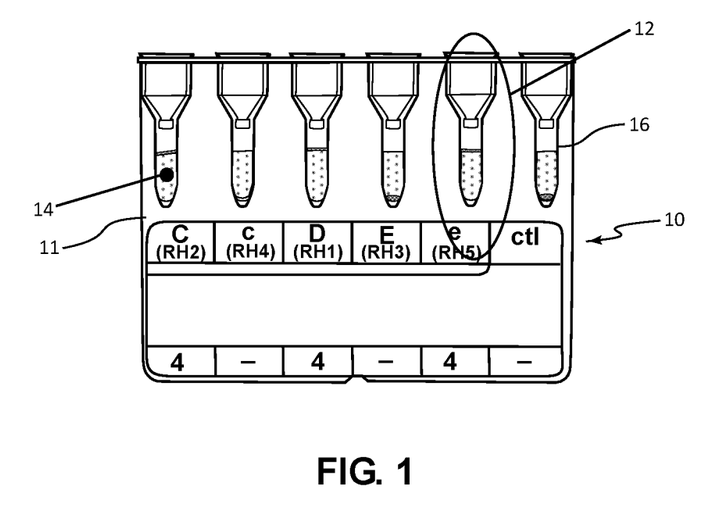
FIG. 1 shows a known gel card.

FIG. 1 is a side view of an exemplary known "gel card" 10 that is made out of plate 11 of transparent plastic that holds together a plurality of transparent plastic containers or "wells" 12 containing each a gel amount 14 and a fluid that may contain a reticulation agent, and optionally a control well 16 containing gel and fluid with no reticulation agent. The gel card is used by introducing a drop of blood sample in each well (and a reagent, if required), incubating the card and then centrifuging the card so that acceleration is directed toward the bottom of the wells of the card. FIG. 1 illustrates an exemplary gel card where the red blood cells agglutinated and remained on top of the first (RH2; C), third (RH1; D) and fifth (RH5; e) wells; or did not agglutinate and fell to the bottom of the second (RH4; c), fourth (RH3; E) and sixth (control) wells.

Figure 2:
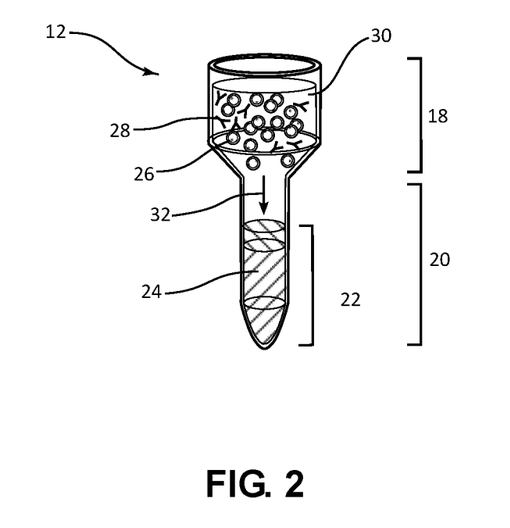
FIG. 2 shows details of a well of the gel card of FIG. 1.
Figure 3A:
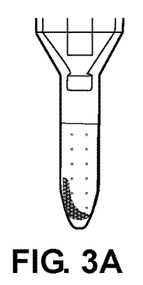
FIGS. 3A to 3F show gel-card wells with atypical reactions.
Figure 3B:
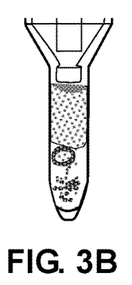
Figure 3C:
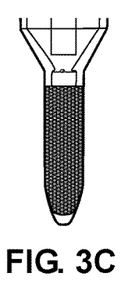
Figure 3D:
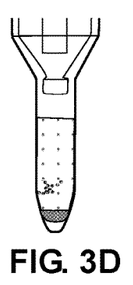
Figure 3E:
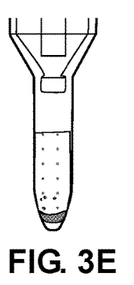
Figure 3F:
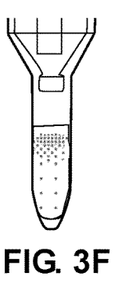

FIG. 2 is an elevation view of a detailed well 12 of card 10; that comprises a top broad incubation chamber 18 for receiving a blood sample to be tested (and a reagent, if required), coupled by a tapered lumen to a bottom narrower well 20 having a tapered lower end; a bottom portion 22 (or reaction chamber) of well 12 being filled with a separation matrix, for example a gel 24, which may contain a reticulation agent. FIG. 2 also shows a blood sample 26 reacting with a reagent 28 in a fluid 30 in chamber 18, before centrifugation of the well 12 pushes 32 the blood sample, reacted or not, toward the bottom of portion 22.

In the past, a human operator was in charge of looking at well 12 after centrifugation and determining if the reaction in the well was positive or negative. However, in order to improve efficiency, some systems were developed to automatically determine if the reaction in the well was positive or negative. Known systems generate a picture of the well, then use image processing software to bring the image to a state where it comprises recognizable features; then to determine using said recognizable features if the reaction in the well was positive or negative.

A problem with image-processing based recognition apparatuses is that if one element of an apparatus is changed, such as the type of camera used to generate the pictures, or the transparency or color of the gel cards, or the type of light used to generate the pictures, the apparatus software must be re-calibrated to amount for any change in the pictures caused by the change of element. Further, image-processing based recognition apparatuses have shown difficulties recognizing atypical reactions as positive or negative.

FIGS. 3A to 3F show pictures of wells with each an atypical reaction that can generally not be recognized by image-processing based recognition apparatuses.

What is needed is an apparatus and/or a method allowing to recognize automatically more atypical reaction pictures, for example of blood agglutination pictures, than the known automated recognition apparatuses and methods; as well as an apparatus and/or a method that does not require re-calibration as often as known recognition apparatuses and/or methods. Embodiments of this presentation address these and other needs.

SUMMARY

An embodiment of this presentation comprises an apparatus for classifying pictures; having a first neural network that receives as distinct inputs each pixel of each color of the input picture, and outputs in return a probability that the picture shows each of a first predetermined series of reactions; and having a second neural network that, if a probability returned by the first neural network for a predetermined reaction is beyond a predetermined level, receives as distinct inputs each pixel of each color of a predetermined portion of the input picture and outputs in return a probability that the picture shows each of a second predetermined series of reactions.

An embodiment of this presentation relates to an apparatus for classifying a picture of a reaction of reactants in a predetermined container; the apparatus comprising: a first neural network arranged for receiving an input picture of a reaction of reactants in a predetermined container and for providing, for each reaction category of a first plurality of reaction categories, a probability that the input picture shows a reaction that belongs to said reaction category of the first plurality of reaction categories; a second neural network arranged for, if the first neural response provides a highest probability that the input picture shows a reaction that belongs to a predetermined reaction category of the first plurality of reaction categories (i.e. if the highest of the probabilities generated by the first neural network relates to said predetermined reaction category of the first plurality of reaction categories), receiving a predetermined portion of the input picture and providing, for each reaction category of a second plurality of reaction categories, a probability that said predetermined portion of the input picture shows a reaction that belongs to said reaction category of the second plurality of reaction categories.

According to an embodiment of this presentation, the apparatus is arranged for issuing a control message indicating that the input picture does not belong to said first plurality of reaction categories if the highest probability issued by first neural network is below a predetermined threshold.

According to an embodiment of this presentation, the apparatus comprises a decision tree arranged for: if the second neural network has not been activated, classifying the input picture as depicting a reaction in the reaction category having the highest probability output by the first neural network; and if the second neural network has been activated, classifying the input picture as depicting a reaction in the reaction category having the highest probability output by the second neural network.

According to an embodiment of this presentation, the apparatus comprises a screening stage; the screening stage having a third neural network arranged for determining: if said input picture is suitable for analysis by the first neural network, in which case the input picture is provided to the first neural network; or if the input picture is not suitable for analysis by the first neural network, in which case the input picture is not provided to the first neural network. According to an embodiment of this presentation, an input picture can be determined as being "non-suitable" if it is recognized by the third network as showing a type of reaction defined to the third network as "non-suitable", and "suitable" otherwise; or reciprocally.

According to an embodiment of this presentation, the third neural network is a neural network trained in a supervised mode by classifying as either suitable or not-suitable each of a plurality of known input pictures of a reaction of reactants in a predetermined container.

According to an embodiment of this presentation, the screening stage comprises a filter arranged to receive the input picture; to generate a picture with reduced information based on the input picture, and to input the reduced information picture in the third neural network.

According to an embodiment of this presentation, the input picture is a color picture and the filter is arranged to transform said color picture in a black and white picture; the third neural network comprising as many single pixel inputs as there are pixels in the black and white picture, where each pixel of the black and white picture is coupled to a pixel input of the first neural network.

According to an embodiment of this presentation, the input picture is a combination of a red input picture, a green input picture and a blue input picture; the first neural network comprising as many single pixel inputs as there are pixels in the red, green and blue input pictures together where each pixel of the red, green and blue input pictures is coupled to a pixel input of the first neural network.

According to an embodiment of this presentation, each single pixel input of the first neural network comprises a predetermined number of single bit inputs.

According to an embodiment of this presentation, the second neural network comprises as many single pixel inputs as there are pixels in the red, green and blue input pictures together of said predetermined portion of the input picture.

According to an embodiment of this presentation, each single pixel input of the second neural network comprises a predetermined number of single bit inputs.

According to an embodiment of this presentation, the first neural network is a neural network trained in a supervised mode by associating to at least one reaction category of said first plurality of reaction categories each of a plurality of known input pictures of a reaction of reactants in a predetermined container.

According to an embodiment of this presentation, said known container is a well of a gel card and said known pictures as well as said input pictures are lateral pictures of a reaction of reactants in a well of a gel card.

According to an embodiment of this presentation, said plurality of known pictures comprise a set of original pictures, each of a different reaction of reactants in a predetermined container and at least one of: a color alteration of said set of original pictures; a mirror image of said set of original pictures; a rotation of the position of said predetermined container in said set of original pictures; a brightness alteration of said set of original pictures; a contrast alteration of said set of original pictures; a blurring of said set of original pictures; a cropping of said set of original pictures; a translation of the position of said predetermined container in said set of original pictures; a scale alteration of said set of original pictures; and said set of original pictures with added noise.

According to an embodiment of this presentation, the second neural network is a network trained in a supervised mode by associating to at least one reaction category of said second plurality of reaction categories said predetermined portion of each of a subset of said plurality of known pictures.

According to an embodiment of this presentation, said known container is a well of a gel card and said known pictures as well as said input pictures are lateral pictures of a reaction of reactants in a well of a gel card; said predetermined portion of said pictures being the portion of the pictures containing the bottom of the well.

Another embodiment of this presentation comprises a container (the container can be a gel card) centrifugation and test device comprising: a centrifugation apparatus arranged for centrifugation of at least one container; an imaging device for generating images of the centrifuged container (for example images of each well of the centrifuged gel card); and an apparatus for classifying a picture of a reaction of reactants in a predetermined container as detailed above, arranged for receiving in input each image of the centrifuged container.

Another embodiment of this presentation relates to a method of programming an apparatus for classifying a picture of a reaction of reactants in a predetermined container as detailed above, the method comprising: training the first neural network in supervised mode with a first series of known pictures and a series of known reaction categories of each said first known pictures; in case at least two reaction categories are not distinguished from each other by the first neural network, grouping said at least two reaction categories as said predetermined category; and training the second neural network in supervised mode with chosen pictures of a second series of known pictures having a known reaction category belonging to said at least two reaction categories (for example chosen pictures of said first series of known pictures), said chosen pictures being cropped to said predetermined portion of the input picture; said predetermined portion of the input picture being an area that emphasizes at least one difference between said at least two reaction categories.

Another embodiment of this presentation relates to a method for classifying a picture of a reaction of reactants in a predetermined container; the method comprising: inputting in a first neural network an input picture of a reaction of reactants in a predetermined container; the first neural network being arranged for providing, for each reaction category of a first plurality of reaction categories, a probability that the input picture shows a reaction that belongs to said reaction category of the first plurality of reaction categories; and if the first neural response provides a highest probability that the input picture shows a reaction that belongs to a predetermined reaction category of the first plurality of reaction categories, inputting in a second neural network a predetermined portion of the input picture; the second neural network being arranged for providing, for each reaction category of a second plurality of reaction categories, a probability that said predetermined portion of the input picture shows a reaction that belongs to said reaction category of the second plurality of reaction categories.

According to an embodiment of this presentation, the method comprises issuing a control message indicating that the input picture does not belong to said first plurality of reaction categories if the highest probability issued by first neural network is below a predetermined threshold.

According to an embodiment of this presentation, the method comprises: if the second neural network has not been activated, using a first decision tree to classify the input picture as showing a reaction in the reaction category having the highest probability output by the first neural network; and if the second neural network has been activated, using a second decision tree to classify the input picture as showing a reaction in the reaction category having the highest probability output by the second neural network.

According to an embodiment of this presentation, the method comprises, before inputting the input picture to the first neural network, inputting said input picture to a third neural network; the third neural network being arranged for determining if the input picture is suitable for analysis by the first neural network; and if the third neural network determines that the input picture is suitable for analysis by the first neural network, implementing said inputting of the input picture in the first neural network; or if the third neural network determines that the input picture is not suitable for analysis by the first neural network, not inputting the input picture in the first neural network.

According to an embodiment of this presentation, the third neural network is a neural network trained in a supervised mode by classifying as either suitable or not-suitable each of a plurality of known input pictures of a reaction of reactants in a predetermined container.

According to an embodiment of this presentation, the method comprises filtering the picture input in the third neural network to reduce the information contained in the picture input to the third neural network.

According to an embodiment of this presentation, the input picture is a color picture and said filtering comprises transforming said color picture into a black and white picture.

According to an embodiment of this presentation, the input picture is a combination of a red input picture, a green input picture and a blue input picture and wherein the first neural network comprises as many single pixel inputs as there are pixels in the red, green and blue input pictures together; said inputting an input picture in a first neural network comprising inputting each pixel of the red, green and blue input picture into a different pixel input of the first neural network.

According to an embodiment of this presentation, the second neural network comprises as many single pixel inputs as there are pixels in the red, green and blue input pictures together of said predetermined portion of the input picture; said inputting a predetermined portion of the input picture in the second neural network comprising inputting each pixel of the red, green and blue predetermined portions of the input picture into a different pixel input of the second neural network.

According to an embodiment of this presentation, the method comprises training the first neural network in a supervised mode by associating to at least one reaction category of said first plurality of reaction categories each of a plurality of known input pictures of a reaction of reactants in a predetermined container.

According to an embodiment of this presentation, said known container is a well of a gel card and said known pictures as well as said input pictures are lateral pictures of a reaction of reactants in a well of a gel card.

According to an embodiment of this presentation, the method comprises forming said plurality of known pictures out of a set of original pictures, each of a different reaction of reactants in a predetermined container and forming at least one of: a color alteration of said set of original pictures; a mirror image of said set of original pictures; a rotation of the position of said predetermined container in said set of original pictures; a brightness alteration of said set of original pictures; a contrast alteration of said set of original pictures; a blurring of said set of original pictures; a cropping of said set of original pictures; a translation of the position of said predetermined container in said set of original pictures; a scale alteration of said set of original pictures; and said set of original pictures with added noise.

According to an embodiment of this presentation, the method comprises training the second neural network in a supervised mode by associating to at least one reaction category of said second plurality of reaction categories said predetermined portion of each of a subset of said plurality of known pictures.

According to an embodiment of this presentation, said known container is a well of a gel card and said known pictures as well as said input pictures are lateral pictures of a reaction of reactants in a well of a gel card; said predetermined portion of said pictures being the portion of the pictures containing the bottom of the well.

These and other features and advantages will become further apparent from the detailed description and accompanying figures that follow. In the figures and description, numerals indicate the various features, like numerals referring to like features throughout both the drawings and the description.

The skilled person understands well that the figures are not necessarily to scale. The figures are presented for illustrative reasons only, and should not be used to restrict the scope of the enclosed claims.

DETAILED DESCRIPTION

In the following description, numerous specific details are set forth to clearly describe various specific embodiments disclosed herein. One skilled in the art, however, will understand that the presently claimed invention may be practiced without all of the specific details discussed below. In other instances, well known features have not been described so as not to obscure the claimed invention.

Figure 4:
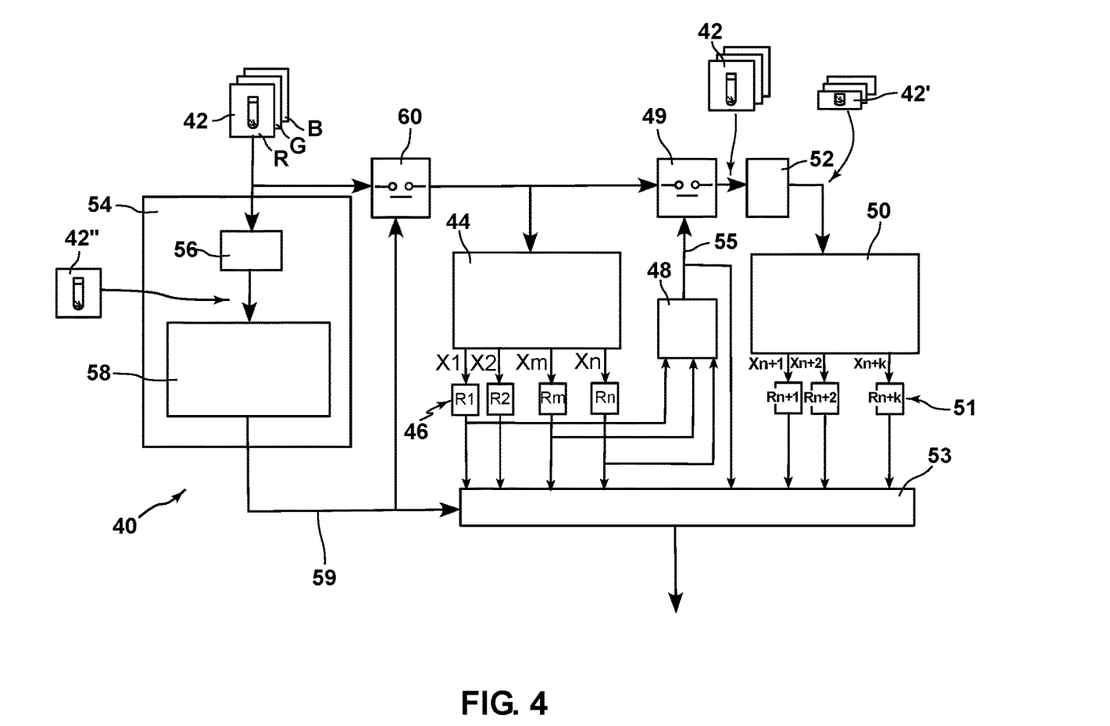
FIG. 4 schematically shows an apparatus according to embodiments of this presentation.

FIG. 4 schematically shows an apparatus 40 according to an embodiment of this presentation, for classifying a picture 42 of a reaction of reactants in a predetermined container, for example a picture of a reaction between a blood sample and agglutination reactant(s) in a gel card well, after centrifugation. According to an embodiment of this presentation, apparatus 40 comprises a first neural network 44 arranged, as detailed hereafter, for receiving an input picture 42 and for providing in return a probability X1 to Xn that the input picture 42 shows a reaction that belongs to each of a first plurality of reaction categories R1 to Rn, respectively. As illustrated in FIG. 4, and as detailed hereafter, picture 42 can be a color picture and it can be comprised of a combination of one red picture R, one blue picture B and one green picture G. According to an embodiment of this presentation neural network 44 is arranged such that each probability X1 to Xn is comprised between 0 and 100%, and the sum of X1 to Xn is 100. According to an embodiment the neural network 44 can also be arranged for outputting an overall reliability of the probabilities X1 to Xn. According to an embodiment of this presentation, values X1 to Xn can be stored in a series 46 of memory buffers R1 to Rn.

According to an embodiment of this presentation, apparatus 40 comprises a first decision circuit 48 arranged for determining if further analysis of picture 42 is required. As detailed hereafter, neural network 44 is arranged such that at least one reaction category Rm among reaction categories R1 to Rn encompasses a plurality of reaction categories that are difficult to distinguish with neural network 44. According to an embodiment of this presentation, decision circuit 48 is arranged for receiving all of the values X1 to Xn, including a value Xm of the chances that picture 42 shows a reaction comprised in reaction category Rm and, if the value Xm is the largest of the values X1 to Xn, for sending (for example via a controlled switch 49 as illustrated in FIG. 4) picture 42 to a second neural network 50.

According to an embodiment of this presentation, a cropping circuit 52 is arranged for receiving the picture 42 sent by decision circuit 48 to the second neural network 50, for extracting a predetermined portion 42' out of picture 42, and for inputting said predetermined portion 42' into the second neural network 50. According to an embodiment of this presentation, cropping circuit 52 is arranged for cropping picture 42 to only its lower portion as illustrated in FIG. 4.

According to an embodiment of this presentation, and as detailed hereafter, the second neural network 50 is arranged for receiving portion 42' of input picture 42 and providing in return a probability Xn+1 to Xn+k that portion 42' shows a reaction that belongs to one of a second plurality of reaction categories Rn+1 to Rn+k, respectively. According to an embodiment of this presentation, values Xn+1 to Xn+k can be stored in a series 51 of memory buffers Rn+1 to Rn+k. According to an embodiment of this presentation, each probability Xn+1 to Xn+k is comprised between 0 and 100%, and the sum of Xn+1 to Xn+K is 100.

According to an embodiment of this presentation, apparatus 40 comprises a second decision circuit 53 arranged for, if the second neural network 50 has not been activated by the first decision circuit 48, classifying input picture 42 as depicting a reaction in the one of categories R1-Rn that has the highest of probabilities X1-Xn output by the first neural network 44; and if the second neural network 50 has been activated by the first decision circuit 48, classifying input picture 42 as depicting a reaction in the one of categories Rn+1-Rn+k that has the highest of probabilities Xn+1-Xn+k output by the second neural network 50. According to an embodiment of this presentation, a control signal 55 generated by decision circuit 48 to control switch 49 can also be used to control the second decision 53 into not taking account the values X1 to Xn if the second neural network 50 has been activated.

According to an embodiment of this presentation, if the first neural response provides a highest probability below a predetermined threshold, a control message such as signal 59 can be sent to the second decision circuit 53, which is can be then arranged to output a message indicating for example that input picture 42 does likely not show a reaction belonging to any of R1-Rn+k.

According to an embodiment of this presentation, apparatus 40 comprises a screening stage 54 that comprises a filter 56 arranged to receive input picture 42 and to generate in return a picture 42" with reduced information. According to an embodiment of this presentation, where picture 42 is a color picture, reduced information picture 42" is a black-and-white picture. According to an embodiment of this presentation and as detailed hereafter, screening stage 54 further comprises a third neural network 58 arranged for determining if input picture 42 is suitable for analysis by first neural network 44, or not. According to an embodiment of this presentation, if neural network 58 determines that input picture 42 is suitable for analysis by first neural network 44, input picture 42 is input into first neural network 44 for example using a controlled switch 60. On another hand, if neural network 58 determines that input picture 42 is not suitable for analysis by first neural network 44, a control message such as signal 59 can be sent to the second decision circuit 53, which can be arranged to output a message indicating for example that input picture 42 does likely not show a reaction belonging to any of R1-Rn+k.

It is noted that FIG. 4 shows a single decision circuit 48 arranged to monitor if the value Xm is the largest of the values X1 to Xn, and eventually to cause second neural network 50 to receive and study a predetermined portion 42' of input picture 42.

However, embodiments of this presentation also provide for having more than one decision circuit 48, each arranged to monitor if a distinct probability Xi is the largest of the values X1 to Xn (each related to a different reaction category Ri) and eventually to cause a different second neural network 50 to receive and study a different predetermined portion 42' of input picture 42. For example, a first predetermined portion 42' of input picture 42 can be the bottom of the picture, as detailed above, whereas a second predetermined portion 42' of input picture 42 can be an intermediate of middle portion of the picture.

Figure 5:
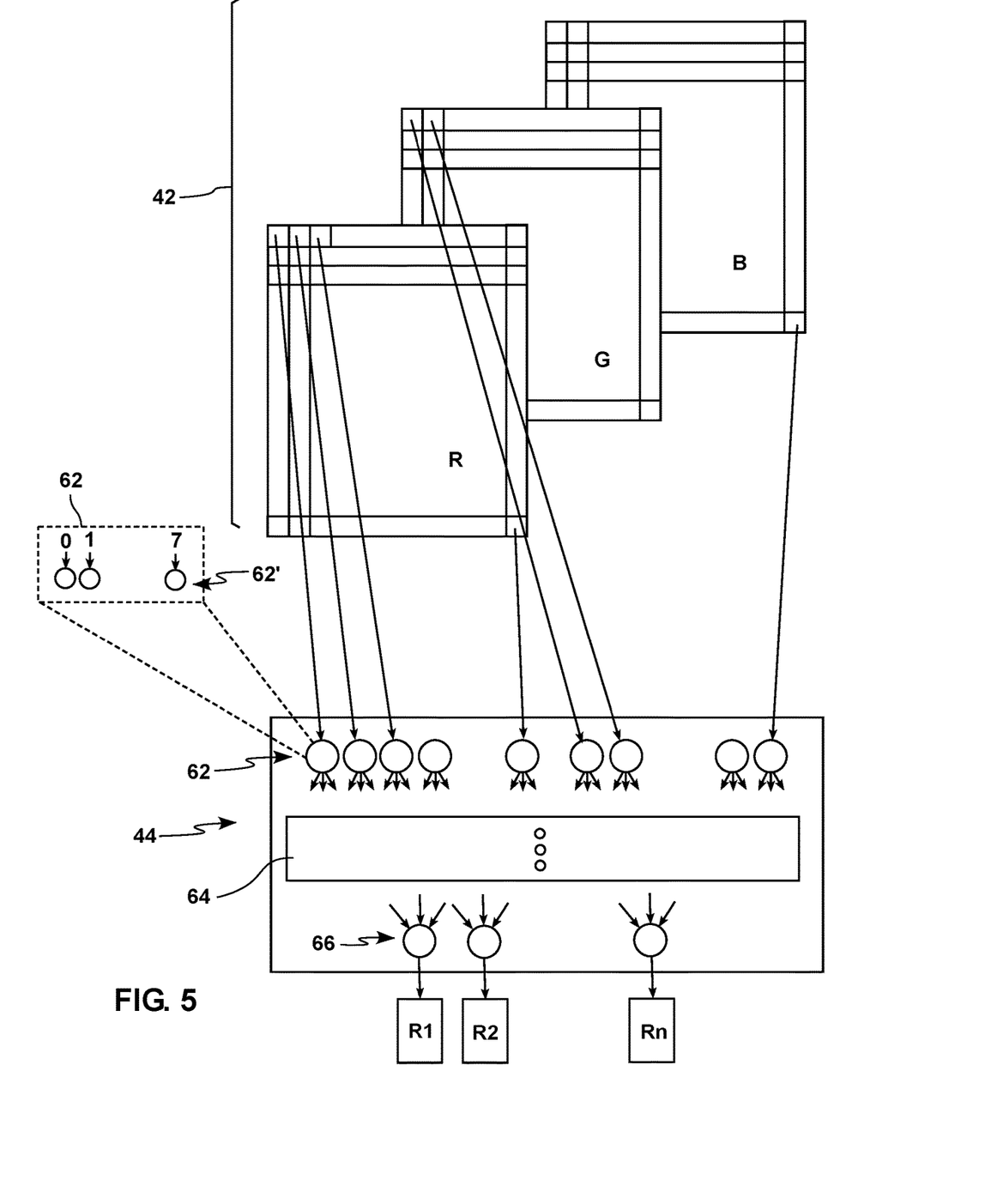
FIG. 5 schematically shows a neural network according to embodiments of this presentation.

FIG. 5 illustrates schematically an embodiment of the first neural network 44 of apparatus 40 and how it receives in input picture 42. According to the illustrated embodiment, neural network 44 comprises an input layer having as many pixel input neurons 62 as there are pixels in all of the red image R, the blue image B and the green image G that form image 42. So if for example each of images R, G and B comprises 50×100=5000 pixels, neural network 44 comprises 15.000 pixel input neurons. Throughout this presentation, the term "neuron" relates to an artificial neuron circuit, implemented either as a dedicated hardware, or as a mix of dedicated hardware and software, or as a software running on a standard programmable hardware such as a computer.

According to an embodiment of this presentation, each pixel input neuron 62 comprises as many single bit neurons 62' as one pixel comprises encoding bits. In the example illustrated in FIG. 5, each pixel of each of the R, G, B pictures that form picture 42 is coded on 8 bits and each pixel input neuron 62 comprises 8 single bit neurons 62' arranged each to receive on its dendrite a binary input. Alternatively, each pixel input neuron 62 can be arranged to receive on its dendrite a single 8-bit encoded pixel signal that can have a value comprised between 0 and 255. According to an embodiment of this presentation, an axon of each pixel input neuron 62 of neural network 44 is connected to a hidden neuron layer 64 that is itself connected to an output neuron layer comprised of output neurons 66, where an axon of each neuron of output layer 66 is coupled to the input of one of memory registers R1 to Rn.

According to an embodiment of this presentation, neural network 44 is trained in a supervised mode by successively inputting a plurality of known pictures to neural network 44, and by each time associating the input known picture to one of reaction categories R1 to Rn. According to an embodiment of this presentation, each picture is a lateral picture of a gel card well after incubation of reactants and after centrifugation. According to an embodiment of this presentation, teaching the neural network requires that a skilled operator recognizes each input known pictures as belonging to a reaction category, and that said category be associated in network 44 to said input known picture. As detailed hereafter however, according to another embodiment of this presentation, teaching the neural network can require that a skilled operator recognizes only a subset of the set of known pictures as belonging to a reaction category, for example when the remainder of the set of known pictures is generated by altering (tilting, changing colors, etc.) the visual appearance of pictures from said subset of the known pictures, whereby the categories of the remainder pictures is already known, despite their altered appearance.

Figure 6:
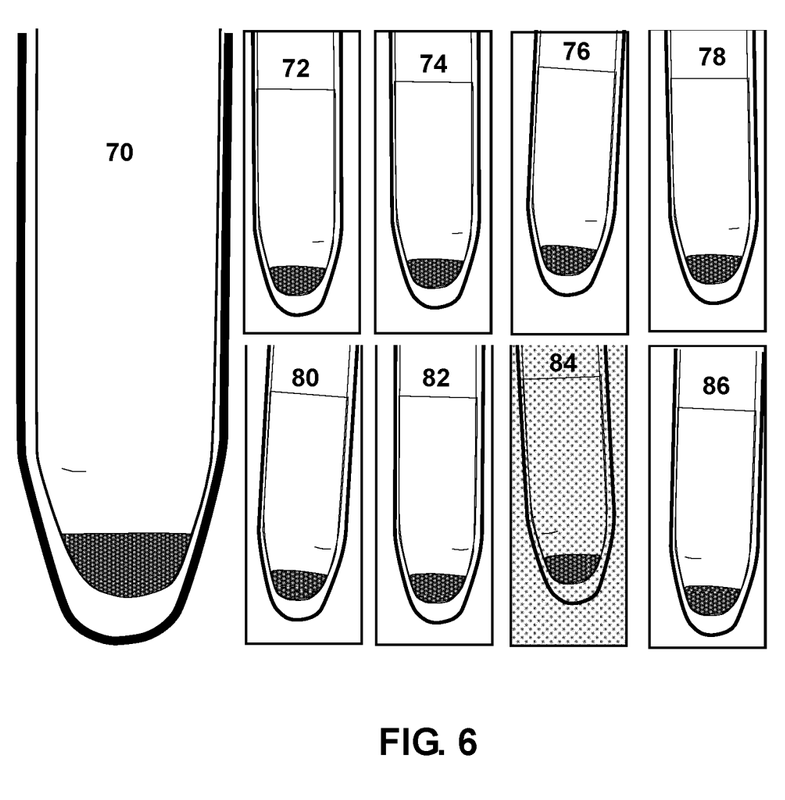
FIG. 6 illustrates in detail how an input picture is processed for training the various neural networks.

FIG. 6 illustrates a method of creating the plurality of known pictures used for training neural network 44 according to an embodiment of this presentation. An original picture 70 is shown. Picture 70 can for example be obtained by a camera such as the camera that will hereafter be used to generate picture 42. According to an embodiment of this presentation, a further picture 72 is formed out of picture 70 by flipping horizontally (mirror image) picture 70. According to an embodiment of this presentation, a further picture 74 is formed out of picture 70 or 72 by making the picture darker and by moving the position of the well vertically. According to an embodiment of this presentation, a further picture 76 is formed out of picture 70 or 72 moving the picture of the well vertically, as well as by rotating the picture of the well by a few degrees. According to an embodiment of this presentation, a further picture 78 is formed out of picture 70 or 72 by making the picture darker and by moving the position of the well vertically and horizontally. According to an embodiment of this presentation, a further picture 80 is formed out of picture 70 or 72 by making the picture darker, moving the picture of the well vertically, and rotating the picture of the well by a few degrees. According to an embodiment of this presentation, a further picture 82 is formed out of picture 70 or 72 by making the picture darker, moving the picture of the well vertically. According to an embodiment of this presentation, a further picture 84 is formed out of picture 70 or 72 by changing the color of the picture, rotating the picture of the well by a few degrees and moving the picture of the well vertically in a manner different from the previous pictures. According to an embodiment of this presentation, a further picture 86 is formed out of picture 70 or 72 by making the picture darker, moving the picture of the well vertically, and rotating the picture of the well by a few degrees in a manner different from the previous pictures.

According to an embodiment of this presentation, the plurality of known pictures used for training neural network 44 is formed, starting from a set of original pictures such as picture 70, by creating additional sets of known pictures such as pictures 72-86 comprising at least one of: a color alteration of said set of original pictures; a mirror image of said set of original pictures; a rotation of the position of said predetermined container in said set of original pictures; a brightness alteration of said set of original pictures; a contrast alteration of said set of original pictures; a blurring of said set of original pictures; a cropping of said set of original pictures; a translation of the position of said predetermined container in said set of original pictures; a scale alteration of said set of original pictures; and said set of original pictures with added noise.

According to an embodiment of this presentation, the additional sets of known pictures can be created automatically by randomly combining any of the picture alterations detailed hereabove.

According to an embodiment of this presentation, since each original picture shows the same reaction as each additional picture generated from said original picture, neural network 44 can be automatically fed all the additional pictures generated from each original picture, and automatically taught that each said additional picture is the same reaction as the reaction (identified by an operator) taught to the neural network for said original picture. The above allows automatically generating a large set of known pictures associated each to a known reaction category out of a reduced size set of known picture individually associated to a known reaction category by a skilled operator.

According to an embodiment of this presentation, once a large set of known pictures associated each to a known reaction category has been generated, neural network 44 can be automatically taught using said a large set of known pictures and their known reaction categories.

According to an embodiment of this presentation, once neural network 44 has been taught, a number of unknown pictures are fed to neural network 44 and the skilled operator verifies that each unknown picture is correctly identified as showing the proper reaction category (by issuing a probability value Xj associated to the proper reaction category Rj larger than the probability values issue for the other reaction categories). If unknown pictures showing pictures of two distinct categories are mis-categorized by neural network 44, network 44 can be additionally trained with additional sets of known pictures as detailed hereabove. If neural network 44 keeps mis-characterizing at least two reaction categories, however, said two reaction categories can be made a single reaction category Rm; whereby neural network 44 issuing a high probability Xm that an input picture 42 belongs to reaction category Rm triggers a detailed analysis by neural network 50 of a predetermined detail/portion 42' of the input picture that shows at least one difference between said at least two categories.

For example, reaction category Rm can be a grouping of a plurality of negative reaction categories that appear distinct to a trained operator but that are not distinguished well by neural network 44. The predetermined portion 42' of the input picture can then for example be as a bottom portion of the input picture, comprising the bottom of the well, where at least one difference between said plurality of negative reaction categories can be found.

FIG. 5 also illustrates the second neural network 50 as well as the first neural network 44, by replacing the reference numbers 44 and 42 with reference numbers 50 and 42' and considering, consistently with the description hereabove relating to neural network 44, that neural network 50 comprises an input neuron layer having as many pixel input neurons as there are pixels in the three portions of red, blue and green pictures that form predetermined picture portion 42'. Also consistent with the description made above for neural network 44, the input neuron layer of neural network 50 is connected to a hidden neuron layer which is itself connected to an output neuron layer; the axon of each output neuron of the output neuron layer being connected to one of the memory registers Rn+1-Rn+k (instead of R1-Rn as illustrated).

The teaching of neural network 50 can be implemented in the same way as the teaching of neural network 44, but using only portions of a set of known pictures picked by an operator as known pictures belonging to (at least) two reaction categories that are not distinguished properly by neural network 44, and that are therefore taught to neural network 44 as being a single reaction category Rm.

Alternatively, according to an embodiment of this presentation, neural network 44 does not need to identify the (at least) two reaction categories that it does not distinguish properly as a single reaction category Rm. However, decision circuit 48 must then be arranged to activate neural network 50 if the output of neural network 44 shows that the input picture belongs (highest probability output) to any one of said (at least) two reaction categories that are not distinguished properly.

As for the teaching of neural network 44, the set of known pictures used for teaching neural network 50 and a corresponding set of known reaction categories can be automatically generated by randomly changing the appearance of a reduced set of original known pictures. As for the teaching of neural network 44, the set of known pictures and their corresponding set of known reaction categories used for teaching neural network 50 can be automatically fed to train neural network 50 once they have been automatically generated from the reduced set of original known pictures.

FIG. 5 also illustrates the third neural network 58 as well as the first neural network 44, by replacing the reference numbers 44 and 42 with reference numbers 58 and 42" and considering, consistently with the description hereabove relating to neural network 44, that neural network 58 comprises an input neuron layer having as many pixel input neurons as there are pixels in the black and white picture 42". Also consistent with the description made above for neural network 44, the input neuron layer of neural network 58 is connected to a hidden neuron layer which is itself connected to a single output neuron; the axon of the output neuron being arranged to provide a signal 59 identifying picture 42 as being suitable or not for analysis by first neural network 44.

The teaching of neural network 58 can be implemented in the same way as the teaching of neural network 44, but using only a set of known black and white pictures having each a single "fit for analysis" or "unfit for analysis" label. According to an embodiment of this presentation, the set of known black and white pictures is generated from a set of known color pictures. According to an embodiment of this presentation, the set of known color pictures can comprise a number of original pictures recognized as showing an identifiable reaction as well as a number of original pictures recognized as not showing an identifiable reaction, as for example pictures having a bubble as FIG. 3B, or an opaque reaction as in FIG. 3C, that do not show an identifiable reaction. Each picture can be associated manually to a label of "fit for analysis" or "unfit for analysis" by an operator. Alternatively, the pictures "unfit for analysis" can be selected automatically or manually from a set of pictures consistently mis-analyzed by the first and second neural networks after training; whereas the pictures "fit for analysis" can be selected automatically or manually from a set of pictures consistently properly analyzed by the first and second neural networks after training.

A set of original black and white pictures can then be formed automatically out of the set of original (fit and unfit) known pictures, and a set of known black and white pictures having each a known label can then be automatically generated for the training of neural network 58 for example by randomly introducing minor alterations in the appearance of the original black and white pictures.

Alternatively, a set of known color pictures having each a fit/unfit label can be formed automatically out of the set of original (fit and unfit) known pictures, for example by randomly introducing minor alterations in the appearance of the original pictures as detailed above, and such set of known color pictures can be fed to neural network 58 in supervised mode through filter 56, which converts in real time each color picture into a black and white picture.

Figure 7:
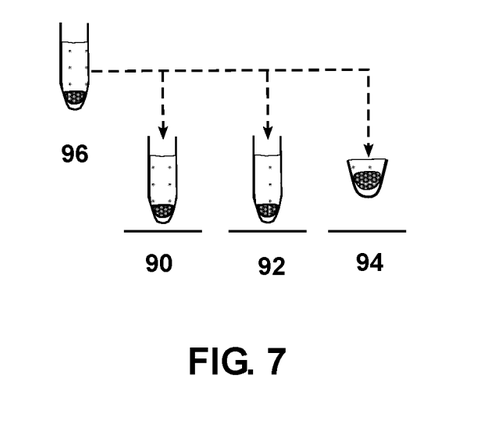
FIG. 7 illustrates in general how an input picture is processed for training the various neural networks.

FIG. 7 illustrates that a set of known black and white pictures 90 for training neural network 58; a set of known color pictures 92 for training neural network 44 and a set of portions of known color pictures 94 for training neural network 50 can be generated out of a single set of original color pictures 96.

Figure 8:
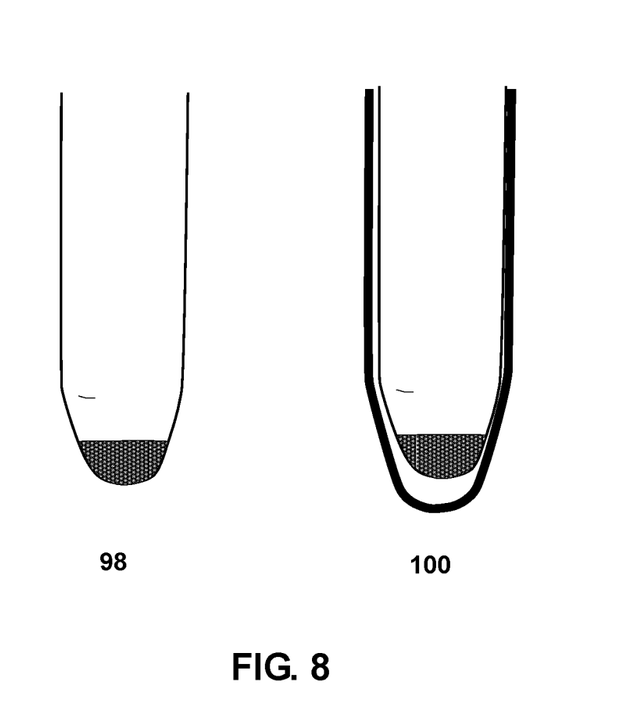
FIG. 8 shows a picture as it must be processed to be recognized by a known picture recognition apparatus, and a picture that can be recognized by an apparatus according to this presentation.

FIG. 8 shows a picture 98 of a blood agglutination gel-card well after centrifugation as it must appear to be classifiable by a known picture recognition apparatus, as well as a picture 100 of a blood agglutination gel-card well after centrifugation as it can appear to be classifiable by a recognition apparatus according to this presentation.

Figure 9:
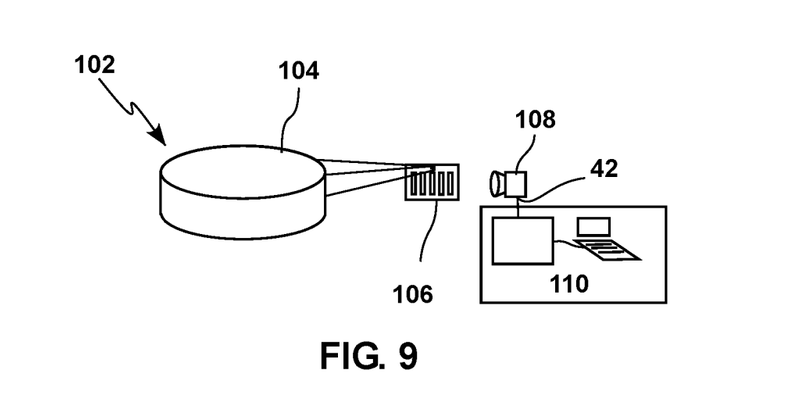
FIG. 9 is a schematic illustration of a gel card centrifugation and test device according to an embodiment of this presentation.

FIG. 9 illustrates a gel card centrifugation and test device 102 according to an embodiment of this presentation, comprising a centrifugation apparatus 104 arranged for centrifugation of at least one gel card 106; an imaging device such as a digital camera 108 for generating images 42 of each well of the centrifuged gel card 106; and an apparatus 110 as shown in FIG. 4 for receiving in input each image 42 of the centrifuged gel cards, and classifying it as showing one of reaction categories R1 to Rm−1 or Rm+1 to Rn or Rn+1 to Rn+k; or as showing an unidentifiable reaction.

It is noted that an apparatus 40 such as shown in FIG. 4 is robust with respect to changes that may occur and cause image 42 to change. For example, a change of optics affecting the color or sharpness or luminosity of picture 42 does not cause picture 42 to be misclassified by apparatus 40. Similarly, an accidental tilt of the gel card when shooting picture 42 does not cause picture 42 to be misclassified by apparatus 40. Further, a change of camera 108 leading to an increase of the number of pixels in image 42 can be handled by cropping the new image to match the original number of pixels such that the well is still part of the cropped picture. Consistently, change of camera leading to a decrease of the number of pixels in image 42 can be handled by stretching the new image to match the original number of pixels.

Having now described the invention in accordance with the requirements of the patent statutes, those skilled in this art will understand how to make changes and modifications to the present invention to meet their specific requirements or conditions. Such changes and modifications may be made without departing from the scope and spirit of the invention as disclosed herein.

The foregoing Detailed Description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. Applicant has made this presentation with respect to the current state of the art, but also contemplates advancements and that adaptations in the future may take into consideration of those advancements, namely in accordance with the current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this presentation is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising the step(s) of . . .".

What is claimed is:

1. An apparatus for classifying a picture of a reaction of reactants in a predetermined container; the apparatus comprising:
    a first neural network arranged for receiving an input picture of a reaction of reactants in the predetermined container and for providing, for each reaction category of a first plurality of reaction categories, a probability that the input picture shows a reaction that belongs to the reaction category of the first plurality of reaction categories;
    a second neural network arranged for, if a first neural response provides a highest probability that the input picture shows a reaction that belongs to a predetermined reaction category of the first plurality of reaction categories, receiving a predetermined portion of the input picture and providing, for each reaction category of a second plurality of reaction categories, a probability that the predetermined portion of the input picture shows a reaction that belongs to the reaction category of the second plurality of reaction categories.

2. The apparatus of claim 1, arranged for issuing a control message indicating that the input picture does not belong to the first plurality of reaction categories if the highest probability issued by the first neural network is below a predetermined threshold.

3. The apparatus of claim 1, further comprising a decision tree arranged for:
    if the second neural network has not been activated, classifying the input picture as depicting a reaction in the reaction category having the highest probability output by the first neural network; and
    if the second neural network has been activated, classifying the input picture as depicting a reaction in the reaction category having a highest probability output by the second neural network.

4. The apparatus of claim 1, further comprising a screening stage, the screening stage having a third neural network arranged for determining:
    that the input picture is suitable for analysis by the first neural network, in which case the input picture is provided to the first neural network; or
    that the input picture is not suitable for analysis by the first neural network, in which case the input picture is not provided to the first neural network.

5. The apparatus of claim 4, wherein the screening stage comprises a filter arranged to receive the input picture, generate a picture with reduced information based on the input picture, and input the reduced information picture in the third neural network.

6. The apparatus of claim 5, wherein the input picture is a color picture and wherein the filter is arranged to transform the color picture into a black and white picture, the third neural network comprising as many single pixel inputs as there are pixels in the black and white picture, where each pixel of the black and white picture is coupled to a pixel input of the first neural network.

7. The apparatus of claim 1, wherein the input picture is a combination of a red input picture, a green input picture, and a blue input picture, the first neural network comprising as many single pixel inputs as there are pixels in the red, green, and blue input pictures together, where each pixel of the red, green, and blue input pictures is coupled to a pixel input of the first neural network.

8. The apparatus of claim 7, wherein each single pixel input of the first neural network comprises a predetermined number of single bit inputs.

9. The apparatus of claim 7, wherein the second neural network comprises as many single pixel inputs as there are pixels in the red, green, and blue input pictures together that correspond to the predetermined portion of the input picture.

10. The apparatus of claim 1, wherein the predetermined container is a well of a gel card and the input picture is a lateral picture of a reaction of reactants in the well of the gel card.

11. The apparatus of claim 10, wherein the first neural network is trained in a supervised mode by associating known input pictures of a reaction of reactants with at least some of the reaction categories, and wherein the known input pictures comprise a set of original pictures, each of a different reaction of reactants and at least one of:
    a color alteration of said set of original pictures;
    a mirror image of said set of original pictures;
    a rotation of the position of said predetermined container in said set of original pictures;
    a brightness alteration of said set of original pictures;
    a contrast alteration of said set of original pictures;
    a blurring of said set of original pictures;
    a cropping of said set of original pictures;

a translation of the position of said predetermined container in said set of original pictures;
a scale alteration of said set of original pictures; or
said set of original pictures with added noise.

12. The apparatus of claim 1, wherein the predetermined container is a well of a gel card and the predetermined portion of the input picture is a portion containing the bottom of the well.

13. A centrifugation and test device comprising:
a centrifugation apparatus arranged for centrifugation of at least one container;
an imaging device for generating images of the container; and
an apparatus of claim 1 for receiving as input the images of the container.

14. A centrifugation and test device according to claim 13, wherein:
the centrifugation apparatus is arranged for centrifugation of at least one gel card;
the imaging device is arranged to generate images of each well of the centrifuged gel card; and
the apparatus of claim 1 is arranged for receiving each image of the centrifuged gel card.

15. A method of programming an apparatus as recited in claim 1, the method comprising:
training the first neural network in supervised mode with a first series of known pictures and a series of known reaction categories of each of the first series of known pictures;
in a case where at least two reaction categories are not distinguished from each other by the first neural network, grouping the at least two reaction categories as the predetermined category; and
training the second neural network in supervised mode with chosen pictures of a second series of known pictures having a known reaction category belonging to the at least two reaction categories, the chosen pictures being cropped to the predetermined portion of the input picture, wherein the predetermined portion of the input picture is an area that emphasizes at least one difference between the at least two reaction categories.

16. A method for classifying a picture of a reaction of reactants in a predetermined container; the method comprising:
inputting in a first neural network an input picture of a reaction of reactants in the predetermined container, the first neural network being arranged for providing, for each reaction category of a first plurality of reaction categories, a probability that the input picture shows a reaction that belongs to the reaction category of the first plurality of reaction categories; and
if a first neural response provides a highest probability that the input picture shows a reaction that belongs to a predetermined reaction category of the first plurality of reaction categories, inputting in a second neural network a predetermined portion of the input picture, the second neural network being arranged for providing, for each reaction category of a second plurality of reaction categories, a probability that the predetermined portion of the input picture shows a reaction that belongs to the reaction category of the second plurality of reaction categories.

17. The method of claim 16, further comprising:
if the second neural network has not been activated, using a first decision tree to classify the input picture as showing a reaction in the reaction category having the highest probability output by the first neural network; and
if the second neural network has been activated, using a second decision tree to classify the input picture as showing a reaction in the reaction category having a highest probability output by the second neural network.

18. The method of claim 6, further comprising:
before inputting the input picture to the first neural network, inputting the input picture to a third neural network, the third neural network being arranged for determining if the input picture is suitable for analysis by the first neural network; and
if the third neural network determines that the input picture is suitable for analysis by the first neural network, implementing said inputting of the input picture in the first neural network; or
if the third neural network determines that the input picture is not suitable for analysis by the first neural network, not inputting the input picture in the first neural network.

19. The method of claim 18, further comprising filtering the picture input in the third neural network to reduce the information contained in the picture input to the third neural network.

20. The method of claim 19, wherein the input picture is a color picture and wherein the filtering comprises transforming the color picture into a black and white picture.

21. The method of claim 16, wherein:
the input picture is a combination of a red input picture, a green input picture, and a blue input picture, and wherein the first neural network comprises as many single pixel inputs as there are pixels in the red, green, and blue input pictures together; and
the inputting of the input picture in the first neural network comprises inputting each pixel of the red, green, and blue input picture into a different pixel input of the first neural network.

22. The method of claim 21, wherein:
the second neural network comprises as many single pixel inputs as there are pixels in the red, green, and blue input pictures together that correspond to the predetermined portion of the input picture; and
the inputting the predetermined portion of the input picture in the second neural network comprising inputting each pixel of the red, green, and blue predetermined portions of the input picture into a different pixel input of the second neural network.

23. The method of claim 16, further comprising training the first neural network in a supervised mode by associating to at least one reaction category of said first plurality of reaction categories each of a plurality of known input pictures of a reaction of reactants in a predetermined container.

24. The method of claim 16, wherein the predetermined container is a well of a gel card and the input picture is a lateral picture of a reaction of reactants in the well of the gel card.

25. The method of claim 24, further comprising forming a plurality of known pictures for training the first neural network out of a set of original pictures, each of a different reaction of reactants in a predetermined container and forming at least one of:
a color alteration of said set of original pictures;
a mirror image of said set of original pictures;

a rotation of the position of said predetermined container in said set of original pictures;
a brightness alteration of said set of original pictures;
a contrast alteration of said set of original pictures;
a blurring of said set of original pictures;
a cropping of said set of original pictures;
a translation of the position of said predetermined container in said set of original pictures;
a scale alteration of said set of original pictures; or
said set of original pictures with added noise.

* * * * *